United States Patent [19]

Higashi et al.

[11] Patent Number: 4,530,906

[45] Date of Patent: Jul. 23, 1985

[54] MICROBIAL RENNET HAVING INCREASED MILK COAGULATING ACTIVITY AND METHOD AND METHOD FOR PRODUCTION THEREOF

[75] Inventors: Toshihiko Higashi, Hachioji; Yoshinori Kobayashi; Shinjiro Iwasaki, both of Hino, all of Japan

[73] Assignee: Meito Sangyo Kabushiki Kaisha, Nagoya, Japan

[21] Appl. No.: 482,171

[22] Filed: Apr. 5, 1983

[30] Foreign Application Priority Data

Apr. 8, 1982 [JP] Japan ................................. 57-57211

[51] Int. Cl.$^3$ .......................... C12N 9/58; C12N 9/96; C12R 1/785
[52] U.S. Cl. .................................... 435/223; 435/188; 435/931
[58] Field of Search .................. 435/223, 188; 426/63

[56] References Cited

U.S. PATENT DOCUMENTS

| 4,255,454 | 3/1981 | Branner-Jorgensen | 426/36 |
| 4,348,482 | 9/1982 | Cornelius | 435/223 |
| 4,357,357 | 11/1982 | Branner-Jorgensen et al. | 435/223 X |
| 4,362,818 | 12/1982 | Cornelius et al. | 435/223 |
| 4,386,160 | 5/1983 | Branner-Jorgensen et al. | 435/221 |

FOREIGN PATENT DOCUMENTS 0027834 6/1981 European Pat. Off. .
WO80/00025 10/1980 PCT Int'l Appl. .

Primary Examiner—Lionel M. Shapiro
Attorney, Agent, or Firm—Wenderoth, Lind & Ponack

[57] ABSTRACT

A method for increasing the milk coagulating activity of microbial rennet obtained from *Mucor pusillus* microorganisms, which comprises acylating the microbial rennet in an aqueous medium by contacting the microbial rennet with succinic anhydride at a temperature of about 0° C. to about 40° C. and a pH of about 4 to about 10 for a time sufficient to obtain the desired increase in milk coagulating activity; and improved microbial rennet having a low PA/MCA index and a high MCA index and obtained by the aforesaid method.

5 Claims, No Drawings

MICROBIAL RENNET HAVING INCREASED MILK COAGULATING ACTIVITY AND METHOD AND METHOD FOR PRODUCTION THEREOF

This invention relates to improved microbial rennet having a low PA/MCA index and a high MCA index and obtained by acylating microbial rennet from *Mucor pusillus* microorganisms with succinic anhydride, and to a method for increasing the milk coagulating activity of microbial rennet from *Mucor pusillus* microorganisms.

In the present specification, "PA" denotes proteolytic activity, and "MCA", milk coagulating activity. The "PA/MCA index" denotes the PA/MCA index of the acylated microbial rennet when the PA/MCA ratio of untreated microbial rennet before acylation is taken as 100. The MCA index denotes the MCA index of the acylated microbial rennet when the MCA of untreated microbial rennet before acylation is taken as 100.

More specifically, this invention pertains to improved microbial rennet having a low PA/MCA index and a high MCA index obtained by acylating microbial rennet from *Mucor pusillus* microorganisms with succinic anhydride, said improved microbial rennet having a proteolytic activity (PA)/milk coagulating activity (MCA) index of from 50 to 90 when the PA/MCA ratio of untreated microbial rennet from *Mucor pusillus* microorganisms before acylation is taken as 100 and a MCA index of more than 100 when the MCA of untreated microbial rennet before acylation is taken as 100.

This invention also relates to a method for increasing the milk coagulating activity (MCA) of microbial rennet obtained from *Mucor pusillus* microorganisms, which comprises acylating the microbial rennet in an aqueous medium by contacting the microbial rennet with succinic anhydride at a temperature of about 0° C. to about 40° C. and a pH of about 4 to about 10 for a time sufficient to obtain the desired increase in milk coagulating activity.

In the classical method of making cheese, rennet (milk-coagulating enzyme) from the fourth stomach of calves is used. In recent years, milk coagulating enzymes serving as substitutes for calf rennet have been developed and come into practical use to cope with the increased consumption of cheese and meat. These milk coagulating enzymes are known as "microbial rennets" and are commercially available.

Rennet is a kind of proteolytic enzyme, and is characterized by having specific proteolytic activity represented by milk coagulating activity (MCA) which cleaves a specified site in K-casein to induce a milk coagulating phenomenon, and non-specific proteolytic activity. The most important property of rennet used for cheese making is that it should have a high MCA and a low PA, that is, a low PA/MCA ratio. High PA/MCA ratios lead to the defect that the yield of the curd is reduced, and there occur troubles in the quality of the resulting cheese, such as bitter taste and poor texture.

The development of microbial rennets was innovative because it removed the bottleneck of supplying calf rennet. In practical applications, however, the microbial rennets had the disadvantage of a higher PA/MCA ratio than calf rennet. Efforts have therefore been made in the past to screen microorganisms capable of producing microbial rennet having a lower PA/MCA ratio. The microbial rennet from *Mucor pusillus* microorganisms as a result of these efforts still has a higher PA/MCA ratio than calf rennet, and it is desired to develop microbial rennet having a lower PA/MCA ratio.

Efforts have also been continued to screen microorganisms capable of producing microbial rennet meeting the above requirement, but no satisfactory result has been obtained as yet.

There has been another technical problem in the field of microbial rennet technology. The whey separated from the curd in the production of cheese using microbial rennet is heat-sterilized and then utilized as an additive for milk-based confectionery and various processed foods. Since, however, known microbial rennet preparations, for example those obtained from *Mucor miehei* microorganisms have high heat stability, they cannot be fully deactivated by heat sterilization. As a result, milk coagulation occurs and the utilization of the whey is undesirably restricted.

In an attempt to solve the above other technical problem, some methods have been proposed to reduce the heat stability of microbial rennet so as to make the whey utilizable.

For example, there have been proposed a method involving treating microbial rennet with hydrogen peroxide or a substance capable of generating hydrogen peroxide (Japanese Laid-Open Patent Publication No. 7092/1980 corresponding to west German OLS No. 2901542), a method involving subjecting microbial rennet to oxidizing the treatment with perchloric acid, perboric acid, perbromic acid, periodic acid, a peroxide, peracetic acid, sodium hypochlorite, etc. (Japanese Laid-Open Patent Publication No. 85286/1981 corresponding to European Patent Application No. 27,834 and Japanese Announced Patent Publication No. 500520/1981 corresponding to International Laid-Open No. WO 80/02225), and a method comprising dye-sensitized photooxidation of microbial rennet (Japanese Laid-Open Patent Publication No. 45192/1981 corresponding to west German OLS No. 3,016,548).

As another attempt at reducing the heat stability of microbial rennet, British Patent Application GB No. 2,038,339A (German OLS No. 2,951,793; corresponding U.S. Pat. No. 4,255,454; Chem. Abst., Vol. 93, p. 277, 127992a) proposed a method for reducing the heat stability of microbial rennet by acylating it with a $C_1$-$C_6$ monocarboxylic acid anhydride.

The above prior patents and other documents do not at all disclose any intention of providing modified microbial rennet having a reduced PA/MCA ratio while retaining the MCA of the untreated microbial rennet (namely at a high ratio of recovery of MCA), nor any intention of reducing the PA/MCA ratio.

With a view to increasing the milk coagulating activity (MCA) of microbial rennet obtained from *Mucor pusillus* microorganisms, U.S. Pat. No. 4,362,818 issued on Dec. 7, 1982 which is after the priority date of the present application proposes a method which comprises acylating the microbial rennet with an acylating agent selected from the group consisting of maleic, citraconic, phthalic, cis-1,2-cyclohexanedicarboxylic, 1,2,4-benzenetricarboxylic, homophthalic, 3-nitrophthalic, bromomaleic and dichloromaleic anhydride. This U.S. Patent shows that acylation with maleic anhydride yielded an enzyme having reduced proteolytic activity.

The U.S. Patent, however, only discloses a method for increasing the milk coagulating activity of microbial rennet obtained from *Mucor pusillus* microorganisms in which the use of the above-specified anhydride of a dior tri-carboxylic acid is essential. It does not refer to succinic anhydride specified in the present invention. The patentee shows that the milk coagulating activity of microbial rennet obtained from *Mucor pusillus* is lost when other similar carboxylic anhydrides such as isatoic anhydrides, trans-1,2-cyclohexanedicarboxylic anhydride, itaconic anhydride, dl-camphoric anhydride and 2,3-dimethylmaleic anhydride are used, and states that acylation of *Mucor pusillus* microbial rennet has a highly selective and unpredictable effect on the enzyme's milk coagulating activity.

The present inventors have made investigations in order to solve the technical problems in the yield and quality of cheese, for example the decrease in the yield of curd and the bitter taste and poor texture of cheese in the making of cheese using microbial rennet. These investigations have led to the discovery that by acylating microbial rennet obtained from *Mucor pusillus* microorganisms with succinic anhydride not referred to in the prior art references including U.S. Pat. No. 4,362,818, there can be provided improved microbial rennet having increased MCA over untreated *Mucor pusillus* microbial rennet before acylation and overcoming the defect of the higher PA/MCA ratio than calf rennet which causes a trouble in utilizing microbial rennet in the making of cheese.

This discovery is quite unexpected in view of the fact that the above-cited U.S. Pat. No. 4,362,818 concludes on the basis of the results of tests on other similar carboxylic anhydrides that the use of the above-specified anhydrides of di- or tri-carboxylic acids is essential and the effect obtained by acylation of *Mucor pusillus* microbial rennet is highly unpredictable.

As is well known, when a protein is treated with maleic anhydride or succinic anhydride, the amino groups in the protein are mainly acylated [see, for example, P. J. G. Butler et al: Methods in Enzymol. 25, 191 (1972), I. M. Klotz: Methods in Enzymol. 11, 576 (1967), and M. A. Qasim et al: Biochim. Biophys. Acta 536, 50 (1978)]. However, the maleylamino group is unstable under acidic conditions and is liable to be split off. For example, P. J. G. Butler et al showed in Biochem. J. 112, 679 (1969) that the maleylamino group is readily hydrolyzed at acid pH and the rate of hydrolysis is directly proportional to the H+ concentration between pH 6 and pH 4.5, and that it has a half life of 11 to 12 hours at a temperature of 37° C. and a pH of 3.5.

The MCA of *Mucor pusillus* microbial rennet is stable at a pH of about 5.0 to about 5.5, and therefore the rennet preparation is usually stored at these pH levels. In the production of cheese utilizing such microbial rennet, it is the usual practice to form a curd by adding the rennet to milk and before separating the curd, cook it at a temperature of, for example, about 38° C. to about 55° C. and a pH of, for example, about 6.4 to about 6.0 for a time of, for example, about 30 to about 60 minutes although these cooking conditions are varied according to the type of cheese to be produced. Furthermore, curing of cheese is sometimes carried out at a pH of about 5.0 to about 5.5 for as long as two years.

In view of the above circumstances, it is likely that during storage and cheese production, the maleyl group will be split off from the *Mucor pusillus* microbial rennet treated with maleic anhydride, and the eliminated maleyl group is subsequently hydrolyzed to maleic acid. It is well known that maleic acid causes troubles such as renal dysfunction, nephron injury and tubular necrosis and induces a symptom very similar to the Fanconi's syndrome [see, for example, R. W. Berliner et al: Proc. Soc. Exp. Biol. Med. 75, 791 (1950), H. E. Harrison et al: Science 120, 606 ((1954), L. E. Rosenberg et al: Biochem. J. 92, 345 (1964), H. J. Kramer et al: J. Lab. Clin. Med. 76, 799 (1970), P. Gmaj et al: Am. J. Physiol. 222, 1182 (1972), H. J. Kramer et al: Nephron 10, 306 (1973), M. Bergeron et al: J. Clin. Invest. 57, 1181 (1976), D. E. Brewer et al: Kidney Int. 12, 244 (1977), A. Gougoux et al: Am. J. Physiol. 231, 1010 (1976), M. Silverman et al.: Am. J. Physiol. 231, 1024 (1976), E. I. Christensen et al: Kidney Int. 17, 771 (1980), M. Szczepanska et al: Am. J. Physiol. 239, F 50 (1980), V. J. Rosen et al: Lab. Invest. 28, 446 (1973), S. F. Wen: Am. J. Physiol. 231, 468 (1976), and R. R. Verani et al: Lab. Invest. 46, 79 (1982).

In the present invention, microbial rennet is succinylated with succinic anhydride. The succinyl group bound to the amino group is much more stable under acidic conditions than the maleyl group bound to the amino group [see, for example, M. H. Klapper et al: Methods in Enzymol. 25, 531 (1972)]. Succinates widely occur in animals and plants, and have long been known as seasonings. For example, Japanese Standards of Food Additives IV (1978), and Food Chemicals Codex, 3rd Edition (1981) from National Research Council, U.S.A. describe succinic acid and its derivatives as food additives. Accordingly, the succinates cause no trouble in regard to safety to man.

It has thus been found that the *Mucor pusillus* microbial rennet acylated with succinic anhydride has much higher stability and safety during storage and cheese production than *Mucor pusillus* microbial rennet acylated with maleic anhydride.

It is an object of this invention therefore to provide improved *Mucor pusillus* microbial rennet having a low PA/MCA index and a high MCA index and exhibiting excellent stability and safety.

Another object of this invention is to provide a method for increasing the MCA of *Mucor pusillus* microbial rennet, which is useful for providing the aforesaid improved *Mucor pusillus* microbial rennet.

The above and other objects and advantages of the invention will become more apparent from the following description.

The starting microbial rennet from *Mucor pusillus* microorganisms used in the production of the improved *Mucor pusillus* microbial rennet of the invention and methods for production thereof are well known, and the above starting microbial rennet is commercially available.

According to the method of this invention, the microbial rennet from *Mucor pusillus* microorganisms is acylated by contacting the rennet with succinic anhydride in an aqueous medium at a temperature of about 0° C. to about 40° C. and a pH of about 4 to about 10 for a time sufficient to obtain the desired increase in the MCA of the rennet.

The acylation can be carried out by contacting the *Mucor pusillus* microbial rennet with succinic anhydride in an aqueous medium. Preferably, the contacting is carried out in the presence of a suitable buffer.

In the practice of the acylation treatment, the conditions for adding succinic anhydride, the type and concentration of the buffer, and the concentration of the starting *Mucor pusillus* microbial rennet can be properly chosen. They can be easily prescribed experimentally according to the desired ratio of decrease in PA/MCA [the balance (expressed in %) obtained by subtracting from 100 the PA/MCA index of the acylated microbial rennet based on the 100 percent PA/MCA ratio of untreated microbial rennet]. Preferably, the acylating treatment is carried out under such conditions that the ratio of decrease of the proteolytic activity (PA)/milk coagulating activity (MCA) ratio of the resulting acylated microbial rennet from the PA/MCA ratio of untreated microbial rennet before acylation is at least about 10%, especially at least about 20%.

The pH of the reaction mixture during the acylation is, for example, about 4 to about 10, preferably about 7 to about 9. Alkalies or acids such as 0.1-4N hydrochloric acid, 5-50 v/v % acetic acid, 0.1-4N sodium hydroxide and 0.1-2M sodium carbonate may be used as pH adjusting agents. The acylation temperature may be about 0° C. to about 40° C., preferably about 0° C. to about 25° C.

The concentration of the starting microbial rennet, in terms of the concentration of protein, is, for example, about 0.1 to about 10 w/v %, preferably about 0.5 to about 3 w/v %. The acylating agent may be added, for example, continuously or batchwise in divided portions to the protein solution rapidly stirred. The amount of the acylating agent added is, for example, about 0.1 to about 2 W/W to protein on a weight basis.

Examples of the buffer that can be used in this invention are 0.05–0.2M sodium acetate buffer, 0.05–0.2M disodium phosphate/citrate buffer, 0.05–0.2M phosphate buffer, 0.1–0.5M sodium bicarbonate/sodium hydroxide buffer, 0.1–0.5M sodium bicarbonate/sodium carbonate buffer, and sodium pyrophosphate buffer.

After the desired acylation, the pH of the reaction mixture is neutralized to a pH of about 5.0 to 6.5 by using a neutralizing agent such as 0.1-4N sodium hydroxide, 0.1-2M sodium carbonate, 0.1-4N hydrochloric acid and 5-50 v/v % acetic acid. If desired, the reaction mixture is subjected to a desalting treatment, for example to dialysis, ultrafiltration or gel filtration to obtain the desired improved *Mucor pusillus* microbial rennet.

In the practice of the method of this invention for increasing the MCA of *Mucor pusillus* microbial rennet, a keeping treatment may be carried out subsequent to the acylating treatment, and it is frequently preferred to complete the acylation treatment in this manner. In this preferred embodiment, the pH of the reaction mixture after acylation with succinic anhydride is adjusted to about 5 to about 6.5, and this reaction mixture having the adjusted pH may be kept at a temperature of about 0° C. to about 50° C. for a time sufficient to obtain the desired increase in MCA.

Preferably, the improved microbial rennet of this invention which can be obtained as above has a PA/MCA index of not more than 90, especially not more than 80, for example 50 to 90, especially 50 to 80, when the PA/MCA ratio of untreated microbial rennet from *Mucor pusillus* microorganisms before the acylating treatment is taken as 100, and a MCA index of more than 100, for example more than 100 to 150, when the MCA of the untreated microbial rennet is taken as 100.

Usually, the improved *Mucor pusillus* microbial rennet of this invention contains at least 4 moles of the succinyl group per mole of the rennet. The amount of the succinyl group may vary depending upon the acylating conditions, etc. For example, it is about 4 to 20 moles.

For example, when the succinyl group is split off from the purified modified microbial rennet by the same method as described in M. H. Klapper et al: Methods in Enzymology, Vol. 25, page 531, 1972 except that hydrolysis is effected with 6N HCl at 100° C. for 48 hours, and the resulting free succinic acid is measured by the method described in J. R. Williamson: Methods of Enzymatic Analysis, Vol. 3, page 1616, Academic Press, New York, 2nd English Edition, 1974, at least 8 moles, for example 8 to 15 moles, preferably 8 to 12 moles, of the succinyl group per mole of the rennet is detected.

Because of its low PA/MCA ratio and high MCA, the improved *Mucor pusillus* microbial rennet can overcome the various troubles encountered in the production of cheese by conventional microbial rennet preparations, such as the reduced yield of the curd, bitter taste and poor texture. It has excellent stability and safety during its storage or its use in the cheese making process. These advantages make the improved *Mucor pusillus* microbial rennet of this invention very useful.

The following Examples illustrate the improved *Mucor pusillus* microbial rennet of this invention and its production more specifically.

In the present invention, PA (non-specific proteolytic activity) and MCA (milk coagulating activity, i.e. specific proteolytic activity) were measured by the following methods.

MCA

Measured in accordance with the method described in S. Iwasaki et al: Agr. Biol. Chem., 31, 546, 1967.

PA

Measured by using a modified method described in R. Fields: Biochem. J. 124, 581, 1971 which involves determining the amino group that has newly appeared as a result of the cleavage of a protein by protease, by using TNBS (2,4,6-trinitrobenzene sulfonate Na salt). The modified method is as follows:

0.1 ml of a test solution is added to 0.4 ml of a dimethylcasein substrate (containing 0.125 W/V % of dimethylcasein in a 50mM disodium phosphate/citrate buffer at a pH of 5.5) pre-heated to 35° C. After reaction at 35° C. for 60 minutes, 2 ml of 0.1M sodium tetraborate/sodium hydroxide (pH 9.5) is added. Then, 1 ml of TNBS reagent (an equal volume mixture of a 0.10 W/V% TNBS solution and 10mM sodium bisulfite) is added to cause color development at 40° C. for 60 minutes. The absorbance ($A_{420}$) at 420 nm is measured using a blank test as a control.

The blank test is carried out by adding 2 ml of 0.1M sodium tetraborate/sodium hydroxide (pH 9.5) to 0.4 ml of the substrate, then adding 0.1 ml of the test solution, and performing the same operation as above.

The measured $A_{420}$ is proportional to the amount of free amono groups formed by the cleaving of the protein by proteolytic activity (PA).

The test solution is used after diluting it accurately to 100 units/ml.

The $A_{420}$ thus represents the PA/MCA ratio.

EXAMPLE 1

This is one example of succinylating *Mucor pusillus* microbial rennet with succinic anhydride. The pH was varied, and its effect on the MCA index (the ratio of recovery of MCA activity) of the succinylated rennet based on 100 MCA of the untreated microbial rennet and the PA/MCA index based on 100 PA/MCA of the untreated microbial rennet was examined.

*Mucor pusillus* was cultivated on a wheat bran medium and the cultivated mass was extracted with tap water. Ethanol was added to the extract and precipitates obtained at an ethanol concentration of 30 to 70 v/v % were dried under reduced pressure to give a rennet powder.

Ten milliliters of a 0.4M solution of $NaHCO_3$ was added to 10 ml of an aqueous solution of the *Mucor pusillus* microbial rennet powder (containing 290 mg of protein and having an MCA of $9.65 \times 10^5$ units) (the protein concentration became 1.45 w/v %, and the $NaHCO_3$ concentration became 0.2M). Then, 2N NaOH was added to the solution to adjust it to each of the pH values shown in Table 1. With stirring at 15° C., 145 mg of succinic anhydride (0.5 w/w based on the protein) was added in five portions at 5 minutes' intervals. After adding the final portion, the reaction was continued for 1 hour. During the reaction, the pH of the reaction mixture was maintained constant as shown in Table 1 using a pH stat. After the reaction, the reaction mixture was adjusted to pH 5.5, and left to stand at 15° C. Sampling was carried out periodically. Each of the samples obtained was diluted with distilled water so that its MCA became about 130 units/ml, and its MCA was measured. Then, the sample was diluted with distilled water so that its MCA accurately became 100 units/ml, and its PA was measured. The results are shown in Table 1.

TABLE 1

Succinylating conditions:
15° C.
anhydride added/protein 0.5 W/W
protein conc. 1.45 W/V %
$NaHCO_3$ conc. 0.2 M

| Run No. | pH at succinyla-tion | Succinylated *M. pusillus* rennet | | | | |
|---|---|---|---|---|---|---|
| | | Percent of original MCA | | | | PA/MCA(*) |
| | | Standing time at pH 5.5, 15° C. | | | | |
| | | 0.5 h | 24 h | 48 h | 72 h | 24 h |
| Control | Non-treated | 100 | 100 | 100 | 100 | 100 |
| 1 | 6.0 | 106 | 108 | 108 | 108 | 84 |
| 2 | 7.0 | 114 | 115 | 116 | 117 | 76 |
| 3 | 8.0 | 102 | 114 | 116 | 117 | 72 |
| 4 | 9.0 | 78 | 111 | 114 | 116 | 72 |
| 5 | 9.5 | 55 | 98 | 112 | 114 | 72 |

(*): Since the PA/MCA ratio hardly changed upon standing for 24 to 72 hours, only the PA/MCA ratio obtained after standing for 24 hours is shown in the table.

Table 1 shows that succinylation increased MCA and reduced PA/MCA. It is also seen that in Runs Nos. 4 and 5 the ratio of recovery of MCA exceeds 100% upon standing after succinylation.

EXAMPLE 2

In this Example, *Mucor pusillus* microbial rennet was succinylated with succinic anhydride at varying temperatures, and the effect of the temperature on the MCA and PA/MCA of the succinylated product was examined.

Succinylation was carried out in the same way as in Example 1 except that the pH at succinylation was adjusted to 7.0. After the final addition of the anhydride, the reaction was continued for 120, 75, 50 and 30 minutes respectively at a succinylation temperature of 0°, 10°, 20° and 30° C. The pH was adjusted to 6.5, and then the reaction mixture was left to stand at 5° C. The results are shown in Table 2.

TABLE 2

Succinylating conditions:
pH 7.0
anhydride added/protein 0.5 W/W
protein conc. 1.45 W/V %
$NaHCO_3$ conc. 0.2 M

| Run No. | Temperature at suc-cinylation | Succinylated *M. pusillus* rennet | | | | |
|---|---|---|---|---|---|---|
| | | Percent of original MCA | | | | PA/MCA |
| | | Standing time at pH 6.5, 5° C. | | | | |
| | | 0.5 h | 24 h | 48 h | 72 h | 24 h |
| Control | Non-treated | 100 | 100 | 100 | 100 | 100 |
| 1 | 0° C. | 83 | 92 | 99 | 103 | 84 |
| 2 | 10° C. | 107 | 110 | 112 | 114 | 77 |
| 3 | 20° C. | 115 | 116 | 118 | 118 | 73 |
| 4 | 30° C. | 117 | 118 | 119 | 119 | 71 |

EXAMPLE 3

In this Example, *Mucor pusillus* microbial rennet was succinylated with varying amounts of succinic anhydride, and the effect of the amount of succinic anhydride on the MCA and PA/MCA of the succinylated product was examined.

Succinylation was carried out in the same way as in Example 1 except that the anhydride was used in each of the amounts indicated in Tables 3-A and 3-B, and the succinylation was carried out at a pH of 8.5 and a temperature of 15° C. (Table 3-A), or at a pH of 7.0 and a temperature of 25° C. (Table 3-B). The anhydride was added in about 30 mg. portions at 5 minutes' intervals, and the reaction was continued for 30 minutes after adding the final portion. Then, the reaction mixture was left to stand at room temperature (20° C. to 25° C.) at a pH of 5.5. The results are shown in Tables 3-A and 3-B.

TABLE 3-A

Succinylation conditions:
pH 8.5, 15° C.
protein conc. 1.45 W/V %
$NaHCO_3$ conc. 0.2 M

| Run No. | Anhydride added/ protein (W/W) | Succinylated *M. pusillus* rennet | | |
|---|---|---|---|---|
| | | Percent of original MCA | | PA/MCA |
| | | Standing time at pH 5.5 and room temperature | | |
| | | 2 h | 24 h | 24 h |
| Control | Non-treated | 100 | 100 | 100 |
| 1 | 0.2 | 92 | 102 | 86 |
| 2 | 0.3 | 104 | 108 | 80 |
| 3 | 0.5 | 106 | 116 | 72 |
| 4 | 0.75 | 106 | 116 | 67 |
| 5 | 1.0 | 104 | 113 | 66 |

TABLE 3-B

Succinylation conditions:
pH 7.0, 25° C.
protein conc. 1.45 W/V %
$NaHCO_3$ conc. 0.2 M

| Run No. | Anhydride added/ protein (W/W) | Succinylated *M. pusillus* rennet | | |
|---|---|---|---|---|
| | | Percent of original MCA | | PA/MCA |
| | | Standing time at pH 5.5 and room temperature | | |
| | | 2 h | 24 h | 24 h |
| Control | Non-treated | 100 | 100 | 100 |
| 1 | 0.25 | 108 | 111 | 74 |
| 2 | 0.5 | 116 | 117 | 72 |
| 3 | 0.75 | 109 | 117 | 71 |

EXAMPLE 4

In this Example, *Mucor pusillus* microbial rennet was succinylated with succinic anhydride using varying concentrations of NaHCO$_3$, and the effect of the concentration of NaHCO$_3$ on the MCA and PA/MCA of the succinylated product was examined.

Succinylation was carried out in the same way as in Example 1 except that the concentration of NaHCO$_3$ was varied as shown in Table 4, the pH at succinylation was adjusted to 8.5, and the amount of the anhydride was 1.0 W/W to protein on a weight basis (ten 29 mg portions of the anhydride were added at 5 minutes' intervals). After the succinylation, the reaction mixture was left to stand at a pH of 6.0 and a temperature of 25° C. The results are shown in Table 4.

TABLE 4

Succinylating conditions:
pH 8.5, 15° C.
anhydride added/protein 1.0 W/W
protein conc. 1.45 W/V %

| | | Succinylated *M. pusillus* rennet | | | | |
|---|---|---|---|---|---|---|
| | | Percent of original MCA | | | | PA/MCA |
| Run No. | NaHCO$_3$ conc. | Immediately after succinylation | Standing time at pH 6.0, 25° C. | | | 24 h |
| | | | 24 h | 48 h | 72 h | |
| Control | Non-treated | 100 | 100 | 100 | 100 | 100 |
| 1 | 0.1 M | 61 | 89 | 96 | 107 | 65 |
| 2 | 0.2 | 74 | 114 | 118 | 121 | 66 |
| 3 | 0.4 | 86 | 119 | 138 | 144 | 69 |
| 4 | 0.6 | 88 | 119 | 142 | 146 | 71 |

EXAMPLE 5

In this Example, *Mucor pusillus* microbial rennet was succinylated with succinic anhydride at various concentrations of the protein, and the effect of the concentration of the protein on the MCA and PA/MCA of the succinylated product was examined.

*Mucor pusillus* was cultivated on a wheat bran medium and the cultivated mass was extracted with tap water. The extract was diluted or concentrated under reduced pressure to obtain an extract having a desired protein concentration. The MCA was about $1.7 \times 10^3$ units per mg of the protein. To 10 ml of the extract was added NaHCO$_3$ powder to make a concentration of 0.1M. The pH of the solution was adjusted to 8.0 with 2N NaOH. With stirring at 15° C., 50 mg of succinic anhydride was added at 5 minutes' intervals so that the anhydride/protein ratio reached 0.4 w/w. After adding the final portion, the reaction was continued for 60 minutes. After the reaction, the reaction mixture was adjusted to pH 6.0 with 50 v/v % acetic acid, and left to stand at 40° C. for 8 hours. The results are shown in Table 5.

TABLE 5

Succinylation conditions:
pH 8.0, 15° C.
anhydride added/protein 0.4 W/W
NaHCO$_3$ conc. 0.1 M

| | | Succinylated *M. pusillus* rennet | |
|---|---|---|---|
| | | Percent of original MCA | PA/MCA |
| Run No. | Protein conc. mg/ml | Immediately after succinylation | After standing at pH 6.0 and 40° C. for 8 hours |
| Control | Non-treated | 100 | 100 | 100 |
| 1 | 12.5 | 74 | 102 | 80 |
| 2 | 25 | 63 | 110 | 78 |
| 3 | 50 | 51 | 108 | 76 |
| 4 | 100 | 44 | 103 | 75 |

EXAMPLE 6

In this Example, *Mucor pusillus* microbial rennet was succinylated with succinic anhydride in the presence of NaCl, and the effect of NaCl on the MCA and PA/MCA of the succinylated product was examined.

Succinylation was carried out as follows:

To the rennet extract having a protein concentration of 50 mg/ml NaCl powder was added to make each of the concentrations as shown in Table 6, and the reaction was carried out at 25° C. and a pH of 8.5. The anhydride added/protein ratio was 0.5 w/w, and the reaction was continued for 30 minutes after adding the final portion of the anhydride. The concentration of NaHCO$_3$ was 0.1M. After succinylation, the reaction mixture was adjusted to pH 5.5, and maintained at 45° C. for 4 hours. The results are shown in Table 6.

TABLE 6

Succinylation conditions:
pH 8.5, 25° C.
anhydride added/protein 0.5 W/W
protein conc. 50 mg/ml
NaHCO$_3$ conc. 0.1 M

| | | Succinylated *M. pusillus* rennet | |
|---|---|---|---|
| | | Percent of original MCA | PA/MCA |
| Run No. | NaCl conc. W/V % | Immediately after succinylation | After standing at pH 5.5 and 45° C. for 4 hours |
| Control | Non-treated | 100 | 100 | 100 |
| 1 | 2 | 68 | 100 | 58 |
| 2 | 4 | 77 | 103 | 59 |
| 3 | 6 | 84 | 101 | 58 |

EXAMPLE 7

In this Example, purified *Mucor pusillus* microbial rennet was succinylated with succinic anhydride.

Purification was carried out by the method described in S. Iwasaki et al: Arg. Biol. Chem. 31, 1421 (1967). The purified *Mucor pusillus* microbial rennet was dissolved in 0.4M NaHCO$_3$/NaOH buffer solution (pH 8.5) so that its concentration reached 1.0 w/v %. To 5 ml of this solution (containing 50 mg of the purified rennet and having a MCA of $2.78 \times 10^5$ units) was added a predetermined amount of succinic anhydride as shown in Table 7 in 5 mg portions at 5 minutes' intervals with stirring at 15° C. After adding the final portion, the reaction was continued for 30 minutes. During the reaction, the pH of the reaction mixture was maintained at 8.5 with 0.1N NaOH using a pH stat. After the reaction, the reaction mixture was adjusted to pH 5.5 with 10 v/v% acetic acid, and then desalted by gel filtration on Sephadex G-25. Then, MCA, PA, the amino group, the succinyl group and the isoelectric point (P$_I$) of the product were measured and determined.

The amino group was determined by the method described in R. Fields: Methods in Enzymol. 25, 464 (1972). The succinyl group was determined by the method described in M. H. Klapper et al: Methods in Enzymol. 25, 531 (1972) except that the succinyl group was cleaved by hydrolysis with 6N HCl at 100° C. for 48 hours, and the freed succinate was determined by the method described in J. R. Williamson: Methods of Enzymatic Analysis, Vol. 3, page 1616, edited by H. V. Bergmeyer, Academic Press, New York, 2nd English Edition, 1974. The results are shown in Table 7.

TABLE 7

Succinylation conditions:
pH 8.5, 15° C.
purified rennet conc. 1.0 W/V %
in 0.4 M NaHCO$_3$—NaOH

| Run No. | Control | Succinylated M. pusillus rennet (purified) | | |
|---|---|---|---|---|
| | | 1 | 2 | 3 |
| Anhydride added/rennet (W/W) | Non-treated | 0.3 | 0.5 | 1.0 |
| Percent of original MCA | 100 | 104 | 113 | 101 |
| PA/MCA ratio | 100 | 79 | 73 | 67 |
| Moles of amino groups reduced/mole | 0 | 6.4 | 8.3 | 10.3 |
| Moles of succinyl groups bound/mole | 0 | 8.3 | 10.2 | 14.9 |
| Isoelectric point (P$_I$) | 3.9 | | | 3.0 |

Table 7 demonstrates that the ratio of recovering MCA activity increased, and the PA/MCA ratio decreased. The results also showed the decrease of the amino group and the introduction of the succinyl group. It is also seen that the introduction of the succinyl group increased a negative charge, and consequently, the isoelectric point (P$_I$) shifted to the acidic side.

What is claimed is:

1. A method for increasing the milk coagulating activity of microbial rennet obtained from *Mucor pusillus* microorganisms, which comprises acylating the microbial rennet in an aqueous medium by contacting the microbial rennet with succinic anhydride at a temperature of about 0° C. to about 40° C. and a pH of about 4 to about 10 for a time sufficient to obtain the desired increase in milk coagulating activity.

2. The method of claim 1 wherein the amount of succinic anhydride is about 0.1 to about 2 by weight to the weight of the protein present in the microbial rennet in the aqueous medium.

3. The method of claim 1 wherein after the acylation, the pH of the system is adjusted to about 5 to about 6.5, and the system having the adjusted pH is kept at a temperature of about 0° C. to about 50° C. for a time sufficient to obtain said desired increase.

4. The method of claim 1 wherein the acylating treatment is carried out under such conditions that the percent decrease of the proteolytic activity/milk coagulating activity ratio of the acylated microbial rennet from that of unreacted microbial rennet before the acylation is at least about 10%.

5. Improved microbial rennet having a low PA/MCA index and a high MCA index and obtained by acylating a microbial rennet from *Mucor pusillus* microorganisms with succinic anhydride, said improved microbial rennet having a proteolytic activity (PA)/milk coagulating activity (MCA) index of 50 to 90 when the PA/MCA ratio of untreated microbial rennet before the acylation is taken as 100, and an MCA index of more than 100 when the MCA of the untreated microbial rennet is taken as 100.

* * * * *

UNITED STATES PATENT AND TRADEMARK OFFICE
CERTIFICATE OF CORRECTION

PATENT NO. : 4,530,906
DATED : July 23, 1985
INVENTOR(S) : Toshihiko HIGASHI, Yoshinori KOBAYASHI, and Shinjiro IWASAKI It is certified that error appears in the above—identified patent and that said Letters Patent is hereby corrected as shown below:

Title page and column 1, line 2,

Please correct the Title from "MICROBIAL RENNET HAVING INCREASED MILK COAGULATING ACTIVITY AND METHOD AND METHOD FOR PRODUCTION THEREOF" to -- MICROBIAL RENNET HAVING INCREASED MILK COAGULATING ACTIVITY AND METHOD FOR PRODUCTION THEREOF -- .

Signed and Sealed this

Fourteenth Day of January 1986

[SEAL]

Attest:

Attesting Officer

DONALD J. QUIGG

Commissioner of Patents and Trademarks